(12) United States Patent
Tielemans

(10) Patent No.: US 6,408,852 B2
(45) Date of Patent: Jun. 25, 2002

(54) ORAL ORTHESIS TO REDUCE SNORING AND SLEEP APNEA SYMPTOMS

(75) Inventor: W. M. J. Tielemans, Maaseik (BE)

(73) Assignee: TNV Research and Development (NL)

( * ) Notice: Subject to any disclaimer, the term of this patent is extended or adjusted under 35 U.S.C. 154(b) by 0 days.

(21) Appl. No.: 09/760,088

(22) Filed: Jan. 11, 2001

Related U.S. Application Data
(60) Provisional application No. 60/175,394, filed on Jan. 11, 2000.

(51) Int. Cl.$^7$ .................................................. A61F 5/56
(52) U.S. Cl. ........................ 128/848; 128/859; 602/902
(58) Field of Search ................................ 128/846, 848, 128/859–862; 602/902

(56) References Cited

U.S. PATENT DOCUMENTS

| | | | | | |
|---|---|---|---|---|---|
| 3,277,892 A | * | 10/1966 | Tepper | ........................ | 128/860 |
| 4,901,737 A | * | 2/1990 | Toone | ........................ | 128/848 |
| 5,915,385 A | * | 6/1999 | Hakimi | ........................ | 128/848 |
| 5,938,436 A | * | 8/1999 | Shevel | ........................ | 128/860 |

* cited by examiner

*Primary Examiner*—Michael A. Brown
(74) *Attorney, Agent, or Firm*—Bierman, Muserlian and Lucas

(57) ABSTRACT

An oral orthesis for reduction of snoring and sleep apnea symptoms.

14 Claims, 2 Drawing Sheets

ORAL ORTHESIS TO REDUCE SNORING AND SLEEP APNEA SYMPTOMS

PRIOR APPLICATION

This application is based on provisional application Ser. No. 60/175,394 filed Jan. 11, 2000.

The invention relates to an oral orthesis for reducing snoring and sleep apnea symptoms comprising a maxilla pallatum plate (1) and, attached thereon, fixing means (2) to fix the plate in the oral cavity and a tongue positioning device (3). Snoring results from the blocking of the airway by the tongue causing the vibrations when air is passed through. In serious occasions, the blocking can cause a temporary lack of oxygen supply to the brain and unconsciousness which may be life threatening.

DE 40 26602 describes such an oral orthesis for preventing snoring. This orthesis has a small maxilla palate plate to which is attached a spring as the tongue position device. The plate is in the form of an arc fitted to the upper row of teeth. The orthesis is anchored in the oral cavity with wires that attach the plate to the teeth. The spring pushes the tongue forward to prevent the blocking of the airway.

SUMMARY OF THE INVENTION

The disadvantage of the known oral orthesis is that it does not sufficiently prevent the blocking of the airway in all circumstances. The object of the present invention therefor is to provide an improved oral orthesis that better prevents snoring and sleep apnea.

This object is achieved, according to the invention, in that the plate 1 extents to cover and support also the soft tissue (1b) of the palate moll.

Surprisingly it was found that the airway is much less blocked and snoring is more effectively prevented. At first, the orthesis creates a larger open airway. Further, it was found that the orthesis according to the invention increases the muscle tonus and thus increases the stiffness of the soft tissue. The stiffer soft tissue does not hang down and close the airway.

Another advantage of the present invention is that it is more comfortable and hence more easily accepted as a measure against snoring. In particular the oral orthesis is more stable anchored in the mouth and does not move with breathing, swallowing etc.

DETAILED DESCRIPTION

Figure 1:
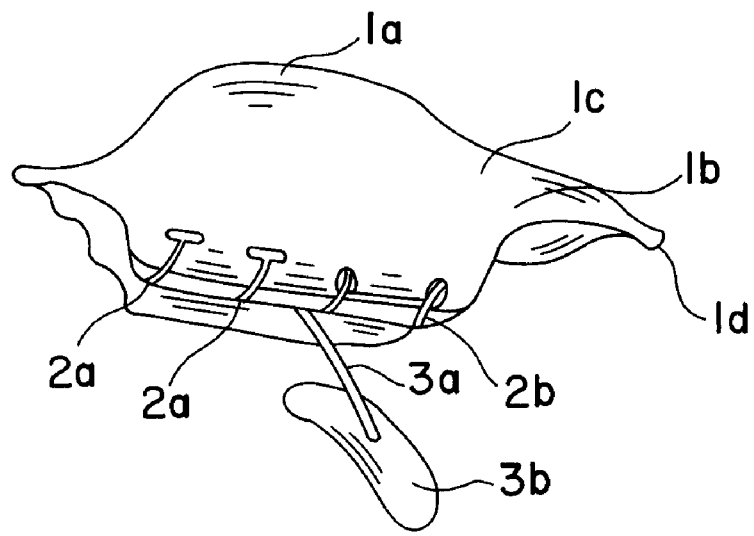
FIG. 1 illustrates a perspective side view of the oral orthesis showing the maxilla palate plate 1 and, attached thereon, fixing means 2 to fix the plate in the oral cavity to the teeth and a tongue positioning device 3. The part of the plate 1a covers the hard part of the palate and part of the plate 1b covers and supports the soft tissue of the palate moll. The spring 3a is mounted in palate 1 and pushes the pellotte 3b against the tongue.
Figure 2:
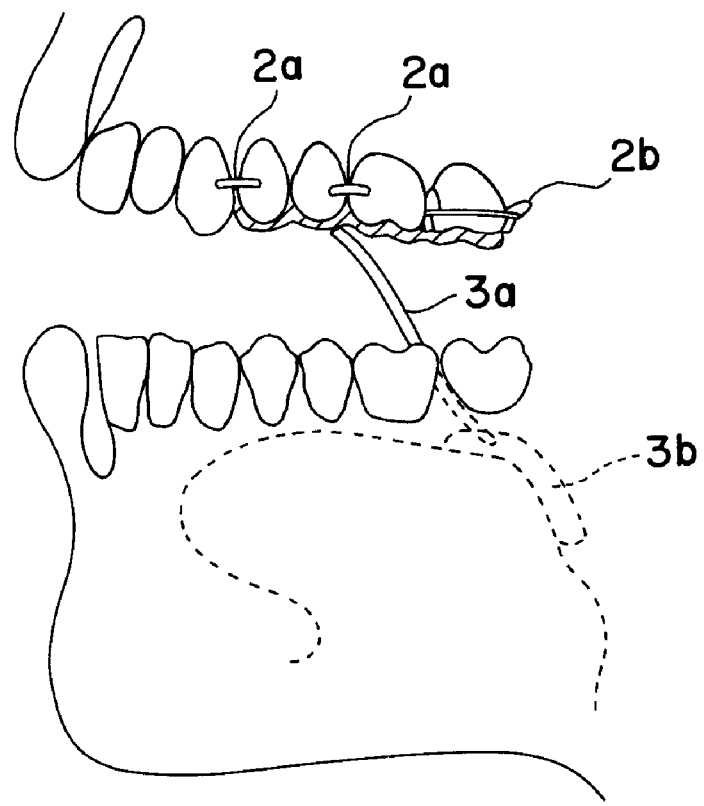
FIG. 2 illustrates the oral orthesis positioned in the oral cavity. The fixing means 2 attach the orthesis to the teeth. The spring 3a pushes against the tongue.
Figure 3:
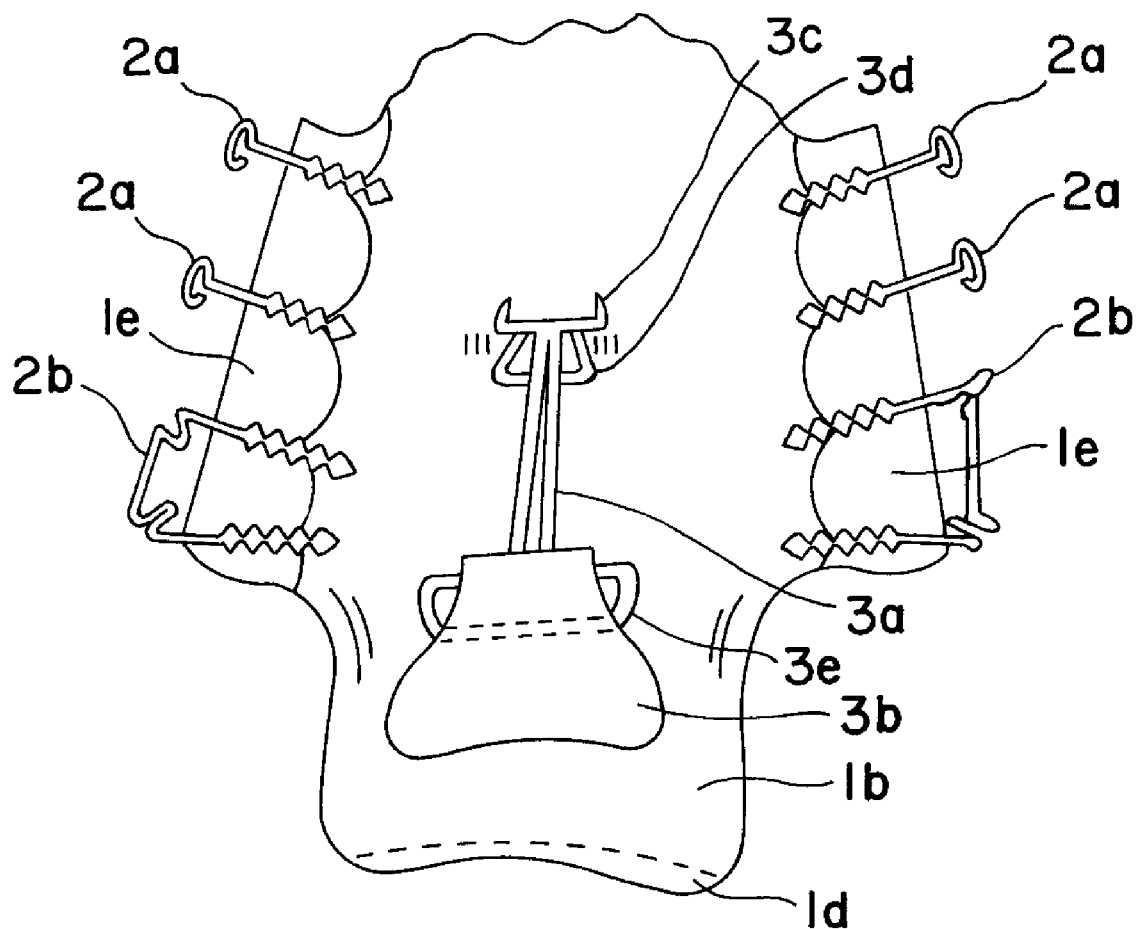
FIG. 3. illustrates a perspective side view of the oral orthesis showing details of the tongue-positioning device 3.

In view of the better opening of the airway and preventing snoring, in the oral orthesis according to the invention, the plate 1 supports preferably at least about 20% of the soft palate (1b). More preferably, it supports at least 30% and more preferably, at least about 40%. The advantage is that the airway is kept more open. In view of wearing comfort preferably at most 60%, preferably at most about 50% of the soft palate are covered.

The inventors found that when the palate moll extends to cover a larger part of the soft tissue the wearing comfort reduces. In view of improving the wearing comfort, in a preferred embodiment of the oral orthesis according to the invention, the plate 1 extents to also support the sensitive area beyond the area where the nerve concentration is high (1c) and the plate 1, at that locus (1c), has an opening or recess to relieve pressure to that sensitive area. The exact location of the area where the nerve concentration is high may differ slightly from person to person but can be easily located by the skilled man.

The oral orthesis according to the invention preferably has in the plate 1, at the dorsal end part, a ridge (1d) to increase the muscle tonus within the soft palate. The advantage of this is that the soft tissue remains harder and does not as easy hang to block the airway.

The oral orthesis according to the invention preferably also has in the plate 1 extension (1e) covering the premolar and/or molar sections. The extensions are molded to fit the profile of the teeth with the mouth in a normal closed relaxed position, for example by casting in a mold formed by biting. These extensions hold in position the lower jaw relative to the upper jaw and prevent to some extent the lower jaw from sliding back and thus closing the airway when the body is in a horizontal position when sleeping.

The plate can be made by methods normally used for dental prosthesis. The plate 1 of the oral orthesis of the invention is preferably made of an acrylic polymer. This polymer has the required stiffness and strength to fix the tongue-positioning device and to exert the force of the spring. In the plate are provided fixing means 2 preferably comprising wire anchoring (2a, 2b) shaped to fix the plate to the molars. The wiring is adapted to fit and anchor to the teeth of the individual using the orthesis as in normal teeth orthesis tongue. The spring wires 3c and 3d are relatively positioned such that sufficient force is applied on the pellotte bar. Preferably the pressing force of the pellotte against the tongue is not more than about 30 g. This can easily be adjusted by the positioning of the spring wires 3c and/or 3d relative to the pellotte bar 3a.

An important feature of the oral orthesis according to the invention is, that the bar (3a) is mounted in the middle of plate 1 and at a distance from the front part between about 0.25 and 0.8 times the length of the plate (as measured along the middle line from the front ridge to the dorsal end ridge). In DE 40 26602 the bar is positioned near the front teeth. Due to this, the pellotte pushes the tongue in more or less vertical direction. The advantage of placing the bar more to the rear, i.e. at more than 0.25 times the length of the plate, is that the tongue is pushed in a direction that is more horizontal, thus more effectively opening the airway.

Is In the oral orthesis according to the invention, preferably the mounting position of bar (3a) In the plate and the length of the bar is chosen in combination such that, with the pellotte (3b) pressed against the tongue in rest position, the bar is at an angle of more than about 30, preferably more than 45, degrees with the plate 1. The movement of the pellotte (3b) operated by the spring (3c, 3d) when in contact with the tongue is preferably predominantly horizontally. The advantage each time is that the airway is more effectively opened.

In view of wearing comfort, the pellotte (3b) is preferably rotatably mounted on an axis (3e) on the bar (3a) to accommodate the movement of the tongue. The rotational movement of the pellotte is preferably blocked when the movement of the pellotte activated by the spring is about horizontal to give a better support and to prevent slipping away of the tongue. Hence in the oral orthesis preferably the pellotte (3b) has means to block rotation of the pellotte relative to the axis (3e) of the bar (3a) over an angle of more than about +/−45 degree such that the spring driven movement of the pellotte is essentially in a horizontal direction. Preferably, the blocking means are provided by protuberances in the pellotte (3b) engaging side arms to axis (3e) of the bar (3a). To prevent slippage of the tongue the pellotte surface may be modified to increase friction, for example by roughening. Preferably the pressing force of the pellotte against the tongue is not more than about 30 g. This can easily be adjusted by the positioning of the spring wires 3c and 3d relative to the pellotte bar 3a.

What is claimed is:

1. Oral orthesis for reducing snoring and sleep apnea symptoms comprising a maxilla palate plate (1) and, attached thereon, fixing means (2) to fix the plate in the oral cavity and a tongue positioning device (3), characterized in that the plate (1) extents to cover and support also the soft tissue (1b) of the palate moll, the tongue positioning device (3) consists of rotatable pellotte (3b) attached to a bar (3a) mounted into the plate with a spring wire (3c and 3d) engaged to press the pellotte against the tongue.

2. Oral orthesis according to claim 1, characterized in that the plate (1) supports at least about 30% of the soft palate.

3. Oral orthesis according to claim 1, characterized in that the plate (1) extents to also support the sensitive area at which the nerve concentration is high and that the plate (1) at that locus (1c) has an opening or recess to relieve pressure to that sensitive area.

4. Oral orthesis according to claim 1, characterized in that the plate (1) has at the dorsal end part a ridge (1d) to increase the muscle tonus within the soft palate.

5. Oral orthesis according to claim 1, characterized in that the plate (1) has extensions (1c) covering the premolar and/or molar sections.

6. Oral orthesis according to claim 1, characterized in that the plate (1) is made of an acrylic polymer.

7. Oral orthesis according to claim 1, characterized in that the fixing means (2) comprises wire anchoring (2a, 2b) shaped to fix the plate to the molars.

8. Oral orthesis according to claim 1, characterized in that the bar (3a) is mounted in the middle of plate (1) and at a distance from the front part between about 0.25 and 0.8 times the length of the plate (as measured along the middle line from the front ridge to the dorsal end ridge).

9. Oral orthesis according to any one of claim 1, characterized in that the mounting position of bar (3a) in the plate and the length of the bar is chosen in combination such that, with the pellotte (3b) pressed against the tongue in rest position, the bar is at an angle of more than about 30, preferably more than 45, degrees with the plate (1).

10. Oral orthesis according to claim 1, characterized in that the movement of the pellotte (3b) operated by the spring (3c, 3d) when in contact with the tongue is predominantly horizontally.

11. Oral orthesis according to claim 1, characterized in that the pellotte (3b) is rotatably mounted on an axis (3e) on the bar (3a) to accommodate the movement of the tongue.

12. Oral orthesis according to claim 11, characterized in that the pellotte (3b) has means to block rotation of the pellotte relative to the axis (3e) of the bar (3a) over an angle of more than about +/−45 degree such that the spring driven movement of the pellotte is essentially in a horizontal direction.

13. Oral orthesis according to claim 12, characterized in that the blocking means are provided by protuberances in the pellotte (3b) engaging side arms to axis (3e) of the bar (3a).

14. Oral orthesis according to claims 1, characterized in that the pressing force of the pellotte against the tongue is not more than about 30 g.

* * * * *